United States Patent [19]

Herkes et al.

[11] Patent Number: 5,491,264
[45] Date of Patent: Feb. 13, 1996

[54] PREPARATION OF ISOPHORONE DIAMINE

[75] Inventors: Frank E. Herkes, Wilmington; Kostantinos Kourtakis, Hockessin, both of Del.

[73] Assignee: E. I. du Pont de Nemours and Company, Wilmington, Del.

[21] Appl. No.: 304,072

[22] Filed: Sep. 12, 1994

Related U.S. Application Data

[63] Continuation-in-part of Ser. No. 94,361, Jul. 27, 1993, abandoned.

[51] Int. Cl.⁶ .................. C07C 209/24; C07C 209/48; C07C 209/52
[52] U.S. Cl. .......... 558/431; 564/446; 564/448; 564/455
[58] Field of Search .................. 564/446, 448, 564/455, 248; 558/431

[56] References Cited

U.S. PATENT DOCUMENTS

| 4,536,577 | 8/1985 | Yoshida et al. | 544/326 |
| 5,371,292 | 12/1994 | Merger et al. | 564/446 |
| 5,395,972 | 3/1995 | Furutani et al. | 564/446 |

FOREIGN PATENT DOCUMENTS

| 2039328 | 3/1991 | Canada. |
| 0394968 | 10/1990 | European Pat. Off.. |

*Primary Examiner*—Glennon H. Hollrah
*Assistant Examiner*—Scott C. Rand
*Attorney, Agent, or Firm*—George A. Frank

[57] ABSTRACT

Isophorone diamine is prepared from isophorone nitrile by imination using a supported heteropoly acid catalyst to form the ketimine followed by the reduction of the ketimine to form the diamine.

3 Claims, No Drawings

PREPARATION OF ISOPHORONE DIAMINE

CROSS REFERENCE TO RELATED APPLICATION

This application is a continuation-in-part of application Ser. No. 08/094,361, filed Jul. 27, 1993, now abandoned.

FIELD OF THE INVENTION

This invention relates to the preparation of 3- aminomethyl-3,5,5-trimethylcyclohexaneamine (isophorone diamine IPDA) from isophorone nitrile (IPN) (also known as 3-cyano-3,5,5,-trimethylcyclohexanone) by imination with ammonia using a supported heteropoly acid catalyst to form the ketimine 3-cyano-3,5,5-trimethyl-cyclohexaneimine (I), followed by reduction of the ketimine I to form isophorone aliamine. The process may be expressed by the equation:

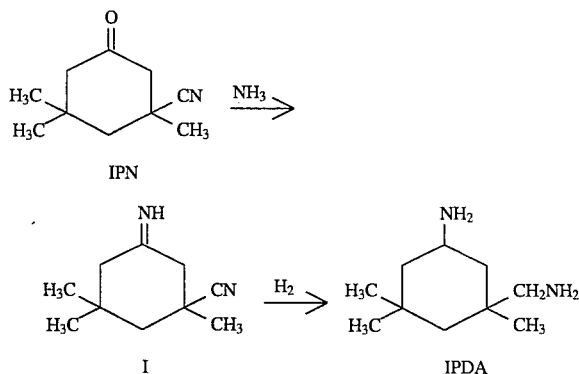

BACKGROUND OF THE INVENTION

3-Aminomethyl-3,5,5-trimethylcyclohexaneamine (isophorone diamine, IPDA) can be prepared continuously by imination of 3-cyano-3,5,5 -trimethylcyclohexanone (isophorone nitrile, IPN) with ammonia to produce a ketimine followed by catalytic hydrogenation. Disteldorf et al., U.S. Pat. No. 4,429,157, discloses the use of an organic ion exchange resin or zeolite as catalysts for the transformation of IPN to the ketimine using liquid ammonia. CA 2,309,328 discloses the use of metal oxide catalysts such as silica, alumina and titanias to perform a similar conversion to the ketimine.

To produce ketimine from a solution of IPN and ammonia requires sufficient residence time and high ammonia/IPN molar ratios to convert IPN to iminated product in a practical manner. For continuous operation of the imination step without catalyst, long reaction times of 120 to 180 minutes at 70° C. and 650 psig, employing molar ratios of ammonia: IPN >6:1 are required for high conversion to the ketimine. The ketimine, however, is not stable if kept in the presence of bases such as aqueous ammonia for long residence times. The ketimine decomposes by the elimination of HCN followed by reactions with IPN and ketimine. This leads to reduced yields of IPDA after the hydrogenation process. Although higher ammonia concentration and lower imination temperature can offset some of the yield losses, shorter imination times are desired to reduce by-product formation. If the imination residence time is reduced, however, unreacted IPN is hydrogenated in the second step to the corresponding amino alcohol product. DE 3,011,656, discloses a process to diminish by-product formation by carrying out the imination in a baffled reactor where backmixing of the fresh feed and reaction product is minimized even though there is longer residence time in the imination reactor. This results in an 85 mol % total IPDA selectivity in the hydrogenated product.

Heteropoly acids are a relatively new class of catalysts having redox properties and strong acidity. The heteropoly acids described here are limited to the Keggin-type. Their acidity is in the same range as that of sulfuric acid and sulfonic acids. U.S. Pat. No. 4,436,577 discloses soluble heteropoly acids used as catalysts for batch imination of 2-alkyl-4-amino-4-formylpyrimidine in methanol. The product aldimine was then catalytically reduced in a subsequent step with ammonia and base to 2-alkyl-5-aminopyrimidine. In this process, no separation or recovery of the catalyst was made, and recovery or recycling of the catalyst difficult, due to its solubility in the product and methanol. If large amount of catalyst is required the process becomes impractical.

CA 2,309,328 discloses the use of metal oxides, which can have both Lewis and Bronsted acidity, as imination catalysts for conversion of IPN to ketimine. Their acidity, however, does not approach that of sulfuric acid, sulfonic acids or strongly acidic ion exchange resins. The latter are not practically useful because of their cost and poor abrasion and thermal stability during the reaction. Metal oxides containing impregnated acid phosphates or sulfates are less stable in the presence of water.

There is a need for an acidic catalyst in the imination process described above which does not go into solution with the product formed; such a catalyst is provided herein by supporting a heteropoly acid on a refractory oxide or carbon such that it remains on the catalyst support during the imination step and provides the same catalytic acidity for the imination step as sulfuric and sulfonic acids without being removed during the imination process where water is produced as a product.

SUMMARY OF THE INVENTION

This invention is a continuous process for the preparation 3- cyano -3,5,5-trimethylcyclohexaneimine I which comprises iminating 3-cyano-3,5,5-trimethylcyclohexanone (IPN) in the presence of excess ammonia at a temperature in the range of 50° to 90° C. at a pressure of 500 to 3500 psig utilizing heterogeneous catalysts prepared by impregnating a heteropoly acid catalyst onto a refractory oxide or carbon support.

This invention further comprises a process for the preparation of IPDA by reducing the imine I with hydrogen and ammonia at elevated temperature and pressure in the presence of a hydrogenation catalyst.

Suitable heteropoly acid catalysts for carrying out the invention include phosphomolybdic acid, phosphotungstic acid, silicomolybdic acid, phosphomolybdotungstic acid and phosphovanadomolybdic acid.

DETAILED DESCRIPTION

Heteropoly acids such as phosphomolybdic acid, phosphotungstic acid, phosphomolybdotungstic acid, phosphovanadaomolybdic acid and silicomolybdic acid when supported on refractory metal oxides such as alumina, silica, titania, niobia, ceria and carbon produce highly stable heterogeneous catalysts which display high catalytic activity for the imination of IPN in the presence of ammonia and water.

Under iminating conditions, the catalysts are highly stable and display catalytic activity similar to sulfonic and sulfuric acids. Moreover, no phosphorous or molybdenum is leached from the support during the imination process. The Keggin-type of heteropolyacids are unique in their catalytic activity; in comparison, phosphoric acid supported on titania or aluminum displays low IPN imination activity.

The heteropoly acids and their salts containing molybdenum, vanadium or tungsten include phosphomolybdic acid, phosphotungstic acid, phosphomolybdotungstic acid, phosphovanadomolybdic acid and silicomolybdic acid. Substoichiometric metal salts such as cesium salts are also active catalysts. The precursor heteropoly acids are generally used as their hydrates. Heteropoly acids with the Keggin structure and their homologs are readily available and are most frequently used as catalysts.

The catalysts for the imination process are prepared by known application techniques such as wet impregnation or incipient wetness (e.g., dry impregnation) using aqueous solutions of the heteropoly acid at room temperature. Solvent application can also be employed using non-reactive solvents such as acetonitrile, methanol or tetrahydrofuran. Typically, the catalysts are used without drying, but can be calcined at a temperature between 100° and 300° C. The concentration of the heteropoly acid on the support can be from 0.1 wt % to 20 wt %, preferably 1 to 6 wt %.

Catalyst levels for the imination process are in the range of 0.2 to 3 grams of catalyst, preferably 0.5 to 2 grams, per grams of IPN plus ammonia and provide sufficient activity to achieve high imination rates.

Suitable supports employed for the heteropoly acids include activated carbon and refractory oxides such as silica, alumina, titania, zirconia, niobia, ceria, tantala and mixtures thereof. Preferably the support is titania. The stoichiometric heteropoly acid metal salts such as with potassium can also be used as a solid catalyst. The supports can be in the form of powders, pellets, spheres and extrudates. The supports are preferably of high purity and surface area, preferably >10 m2/g.

The imination process can be carried out in any suitable reactor such as a batch, continuous fixed-bed, slurry or fluidized bed with ammonia in molar ratios of 6 to 100, preferably 10–30, per mole of IPN. Preferably the reactor is a continuous fixed-bed type. Imination temperatures can range from 40° to 90° C., with 50° to 80° C. preferred. The imination pressure is that required to maintain ammonia mainly in the liquid state at the imination temperature and can range from 300 to 3500 psig. Reactor residence times are 1 to 90 minutes with 10–30 minutes preferred.

The reduction of the ketimine I to isophorone diamine (IPDA) using hydrogenation catalysts is disclosed in Disteldorf et al., 4,429,157 at temperatures in the range of 80° to 200° C. and pressures in the range of 80 to 300 bar. Conventional hydrogenation catalysts such as Group VIII metals and Raney® catalyst can be used.

EXAMPLE 1

Continuous Preparation of IPDA

Step A: $H_3PMo_{12}O_{40}$ (13.69g) was weighed in a dry box to avoid excessive hydration of the acid. The acid was dissolved in 24 ml of deionized water at room temperature. Three hundred grams of titania pellets (⅛ in×⅛ in, surface area=45.3 $m^2$/g, PV=0.14 cc/g) was sprayed with the aqueous solution to allow uniform absorption of the liquid into the pores of the pellet. While spraying, the support was agitated on open pans to promote a uniform coating. The catalyst was then used as prepared, without further washing or drying.

Step B: Into a vertical stainless steel fixed bed continuous flow reactor (41 in.×0.69 in. diameter; electrically heated) was charged 314 g of catalyst containing 4.4 wt % (on a dry basis) 12-molybdophosphoric acid ($H_3PMo_{12}O_{40}$) supported on titania pellets (⅛ in. diameter, 141 $m^2$/g surface area) prepared as in Step A. A second vertical tubular hydrogenation reactor (36 in.×1 in. diameter) in series was charged with Raney cobalt catalyst (200 cc) and glass beads. Liquid ammonia (330g/hr) and isophorone nitrile (99%, 136 g/hr) were pumped continuously downflow through the first reactor at 60° and 238 bar pressure. The hold-up-time in the imination step was 9 minutes.

The ketimine product in ammonia exiting the first reactor was then fed into the top of a hydrogenation reactor at 110° C. and 238 bar along with 74 L/hr hydrogen. The hydrogenated product was passed through a high pressure separator to remove hydrogen followed by a low pressure separator to remove ammonia. Gas chromatographic analysis of the product indicated 92.2 wt % isophorone diamine, 4.9 wt % 1,3,3-trimethyl-6-azabicyclo-[3.2.1]-octane, 0.85 wt % 3-aminomethyl-3,5,5,-trimethylcyclohexanol, 2.8 wt % isophorone aminonitrile and 0.17 wt % low boilers.

In a comparison reaction, but in the absence of imination catalyst under similar reaction conditions and a 16-minute imination residence time, the product analysis showed only 73.5 wt % isophorone diamine, 3.1 wt % 1,3,3-trimethyl-6-azabicyclo-[3.2.1]-octane, 22.0 wt % 3-aminomethyl-3,5,5-trimethylcyclohexanol, 0.91 wt % isophorone aminonitrile and 0.37 wt % low boilers. Here the isophorone yield was considerably lower and by-product formation of 3-aminomethyl-3,5,5-trimethylcyclohexanol was approximately 22 times higher.

EXAMPLE 2

Continuous Imination and Hydrogenation of IPN using $H_3PMo_{12}O_{40}$ Supported on Titania Into a vertical stainless steel fixed bed continuous flow reactor (41 in.×0.69 in. diameter; electrically heated) was charged 248 cc catalyst containing 4.4 wt % (dry basis) 12-molybdophosphoric acid ($H_3PMo_{12}O_{40}$) supported on titania pellets ⅛ in. diameter, 141 $m^2$/g surface area). A second vertical tubular hydrogenation reactor (36 in.×1 in. diameter) in series was charged with Raney ® cobalt catalyst (200 cc) and glass beads. Liquid ammonia (229 g/hr) and isophorone nitrile (99%, 51 g/hr) were pumped continuously downflow through the first reactor at 70° C. and 238 bar pressure. The hold-up-time in the imination step was 16 minutes.

The ketimine product in ammonia exiting the first reactor was then fed into the top of the hydrogenation reactor at 129° C. and 238 bar along with 43 L/hr hydrogen. The product was passed through a high pressure separator to remove hydrogen followed by a low pressure separator to remove ammonia. Gas chromatographic analysis of the product showed 93.2 wt % isophorone diamine, 4.3 wt % 1,3,3-trimethyl-6-azabicyclo-[3.2.1]-octane, 0.42 wt % 3-aminomethyl -3,5,5,-trimethylcyclohexanol, 1.1 wt % isophorone aminonitrile and 0.86 wt % low boilers.

EXAMPLE 3

Batch Imination of IPN

STEP A

Preparation of Catalyst on Carbon $H_3PMo_{12}O_{40}$ (23g) was dissolved in 30 ml deionized water. Fifty grams of an acid-washed carbon (surface area= 677 m$^2$/g) was added to the solution at room temperature to produce an active supported catalyst.

STEP B

Preparation of Catalysts on Niobium and Tantalum Oxides

The oxides of niobium and tantalum were prepared from the corresponding ethoxide derivative by hydrolysis with water.

$H_4PMo_{11}VO_{40}$ was prepared by refluxing 288.01 g $MoO_3$, 24.98 g 85% $H_3PO_4$, 16.53g $V_2O_5$ with 1000 ml deionized water for 165 hrs. This produced a stock solution of 317.86 g $H_4PMo_{11}VO_{40}$ in water. Fifteen milliliters of this solution (containing 4g of the heteropoly acid) was added to a hydrolyzed solution of 86.21 g niobium ethoxide (or 98.11 g tantalum ethoxide) in water.

STEP C

Into a 300-cc stainless steel batch autoclave were charged 50 grams (99%, 0.30 mole) of isophorone nitrile and 5 grams of 3.6 wt % $H_xCs_{1.5}P_{1.2}Mo_{12}O_{40}$ supported on titania powder (surface area=10.3 m2/g surface area) at 25° C. The reactor was sealed and pressured to 14 bar with $N_2$. Liquid ammonia (103 g, 155 ml; 6.24 moles) was added from an Isco pump in series with an inverted ammonia cylinder. The reactor was bled several times to remove excess $N_2$ pressure as the ammonia was added. A pressure of 17 bar was maintained throughout the addition at 25° C. The reactor was heated to 70° C. and slow (500 rpm) stirring commenced. A final pressure of 44 bar was maintained throughout the imination step. Samples (approximately 2 ml) were taken every 15 minutes and dissolved in 200 ml of tetrahydrofuran followed by analysis using gas chromatography. After 15 minutes, 98.2% conversion of IPN to the ketimine (I) was observed. Further samples through 90 minutes all showed a 98% conversion to the ketimine.

Similar batch iminations were performed using similar weights of catalyst, ammonia and IPN. Examples of these catalysts (including their surface areas, SA) and conversions to the desired ketimine are summarized in the Table below:

| Catalyst | Loading (wt %) | Support SA = m$^2$/g | Conv. (%) | Time (min.) |
|---|---|---|---|---|
| $H_3PMo_{12}O_{40}$ | 6.78 | titania (45) | 96.9 | 15 |
| $H_3PWo_{12}O_{40}$ | 3.2 | ceria (68) | 96.9 | 15 |
| $H_4PMo_{11}VO_{40}$ | 9.1 | tantala | 95.6 | 15 |
| $H_xCs_{1.5}P_{1.2}Mo_{12}VO_{40}$ | 3.6 | titania (10.3) | 98.2 | 15 |
| $H_xCs_{1.5}P_{1.2}Mo_{12}VO_{40}$ | 20 | silica (221) | 96.0 | 15 |
| $H_3PMo_{12}O_{40}$ | 5.7 | silica (221) | 97.1 | 15 |
| $H_3PMo_{12}O_{40}$ | 23.2 | carbon (677) | 96.0 | 15 |
| $H_3PMo_{12}O_{40}$ | 6.9 | alumina (100.2) | 97.0 | 30 |
| $H_3PMo_{12}O_{40}$ | 2.1 | ceria (68) | 96.3 | 15 |
| $H_4PMo_{11}VO_{40}$ | 9.1 | niobia | 98.3 | 15 |
| $H_4SiMo_{12}O_{40}$ | 4.4 | titania | 92 | 30 |
| $H_3PMo_{12}O_{40}$ | 100 | none | 96.9 | 15 |

As can be seen from the data, the heterogeneous catalysts containing heteropolyacids can also be employed for batch iminations and can be reused for further iminations due to their insolubility in the reaction medium. In contrast, although unsupported heteropoly acid catalyzes the imination reaction (see data in last line of Table), it cannot be separated from the imine product and, therefore, cannot be used in continuous processes.

EXAMPLE 4

Batch Imination of IPN using Titania (Comparative Example)

Into a 300-cc stainless steel batch autoclave was charged 50 grams (99%, 0.30 mole) of isophorone nitrile and 5 grams of titania (surface area=10.3 m$^2$/g). There was no heteropoly acid catalyst added. The reactor was sealed and pressured to 14 bar with $N_2$. Liquid ammonia (1 03g, 155 ml; 6.24 moles) was added from an Isco pump in series with an inverted ammonia cylinder. The reactor was bled several times to remove excess $N_2$ pressure as the ammonia was added. A pressure of 17 bar was maintained throughout the addition at 25° C. The reactor was heated to 70° C. and slow (500 rpm) stirring commenced. A final pressure of 44 bar was maintained throughout the imination step. Samples (approximately 2 ml) were taken every 15 minutes and dissolved into 200 ml tetrahydrofuran followed by analysis using gas chromatography. After 30 minutes, 82.3% conversion of IPN to the ketimine (I) was observed. Samples taken after 60 and 90 minutes indicated a 92.9% and 95.2% ketimine conversion, respectively. These reaction times are 6 times slower than those observed when heteropoly acid catalysts supported on titania of this invention were used.

Example 5

Preparation of IPDA

To a 300-cc batch autoclave was charged 150 ml of a tetrahydrofuran solution of IPN prepared using a $H_3PMo_{12}O_{40}$ on $TiO_2$ catalyst (93.2% IPN ketimine on a solvent free basis) and 1.2 g Cr-promoted Raney® Co catalyst. The reactor was sealed and purged three times with hydrogen followed by 14 g ammonia addition under 3.4 bar pressure. Minimal stirring was applied during heat-up to 50° C. The pressure was raised to 14 bar with hydrogen and maximum stirring commenced. After four hours, the reaction was stopped, cooled and the product filtered away from the catalyst. Gas chromatographic analysis of the product showed 73% conversion of the ketimine. Product composition (solvent free basis) was 48.3% isophorone diamine, 2.3% 3,3,5-trimethylcyclohexylamine, 1.3% 1,3,3-trimethyl-6-azabicyclo[3.2.1]-octane, 14.3% 1,3,3-trimethyl-5-aminocyclohexanecarbonitrile and 24.9% IPN ketimine (I).

We claim:

1. A continuous process for the preparation of 3-cyano-3,5,5-trimethylcyclohexaneimine which comprises the treatment of 3-cyano-3,5,5-trimethylcyclohexanone (IPN) with ammonia in a molar ratio of 6–100 moles of ammonia per mole of IPN, at a temperature in the range of 50° to 90° C.

and at a pressure in the range of 500 to 3500 psig, in the presence of 0.2–3 grams of a heteropoly acid catalyst supported on a refractory oxide or carbon per gram of IPN plus ammonia, wherein the catalyst remains on the support throughout the process.

2. A continuous process for the preparation of 3-(aminomethyl)-3,5,5-trimethylcyclohexaneamine comprising the steps of A. treatment of 3-cyano-3,5,5-trimethylcyclohexanone (IPN) with ammonia in a molar ration of 6–100 moles of ammonia per mole of IPN, at a temperature in the range of 50° to 90° C. and at a pressure in the range of 500 to 3500 psig, in the presence of 0.2–3 grams of a heteropoly acid catalyst supported on a refractory oxide or carbon per gram of IPN plus ammonia, wherein the catalyst remains on the support throughout the process; and B. reducing the imine produced in step (A) above at elevated temperature and pressure in the presence of hydrogen, ammonia and a hydrogenation catalyst.

3. The process of claim 1 wherein the heteropoly acid catalyst is selected from the group consisting of phosphomolybdic acid, phosphotungstic acid, silicomolybdic acid, phosphomolybdotungstic acid and phosphovanadomolybdic acid.

* * * * *